United States Patent [19]

Wallshein

[11] 4,323,345
[45] Apr. 6, 1982

[54] ORTHODONTIC BIASSING DEVICE WITH SCREW DISENGAGEMENT PREVENTING MEANS

[76] Inventor: Melvin Wallshein, 8645 Bay Pkwy., Brooklyn, N.Y. 11214

[21] Appl. No.: 95,378

[22] Filed: Nov. 19, 1979

Related U.S. Application Data

[62] Division of Ser. No. 785,587, Apr. 7, 1977, Pat. No. 4,200,979.

[51] Int. Cl.³ .............................................. A61C 3/00
[52] U.S. Cl. .......................................... 433/7; 254/98
[58] Field of Search .................... 433/7, 177; 254/102, 254/67, 98, 100, 103

[56] References Cited

U.S. PATENT DOCUMENTS

| | | | |
|---|---|---|---|
| 989,035 | 4/1911 | Parker et al. | 254/102 |
| 1,559,045 | 10/1925 | McColley | 254/100 |
| 1,593,217 | 7/1926 | Lucker | 254/103 |
| 2,080,530 | 5/1937 | Brush | 254/100 |
| 2,266,860 | 12/1941 | Griesinger | 433/7 |
| 2,310,942 | 2/1943 | Donges | 254/100 |
| 3,284,902 | 11/1966 | Dillberg et al. | 433/7 |
| 3,835,540 | 9/1974 | Biederman | 433/7 |
| 4,107,843 | 8/1978 | Spino et al. | 433/7 |

FOREIGN PATENT DOCUMENTS

| | | | |
|---|---|---|---|
| 846001 | 6/1952 | Fed. Rep. of Germany | 433/7 |
| 831155 | 10/1938 | France | 433/7 |
| 986642 | 10/1951 | France | 433/7 |
| 998076 | 1/1952 | France | 433/7 |
| 56338 | 9/1952 | France | 433/7 |
| 58114 | 9/1953 | France | 433/7 |
| 1206848 | 2/1960 | France | 433/7 |
| 1373181 | 10/1964 | France | 433/7 |
| 483374 | 4/1938 | United Kingdom | 433/7 |
| 668227 | 3/1952 | United Kingdom | 433/7 |
| 980322 | 1/1965 | United Kingdom | 433/7 |
| 1049331 | 11/1966 | United Kingdom | 433/7 |
| 1480373 | 7/1970 | United Kingdom | 433/7 |

*Primary Examiner*—Gene Mancene
*Assistant Examiner*—John J. Wilson
*Attorney, Agent, or Firm*—Frishauf, Holtz, Goodman and Woodward

[57] ABSTRACT

Orthodontic biassing devices including various means for preventing screw actuators from becoming disengaged from the body member in which it is cooperatively threadably engaged. The disengagement preventing means may include means directly associated with the screws, and/or stabilizing and retaining rod-like members which are slideably engaged with at least one of the body members of the biassing device. Further disclosed is a means for preventing screws of biassing devices from being backed into the body members due to external pressures applied thereto.

56 Claims, 29 Drawing Figures

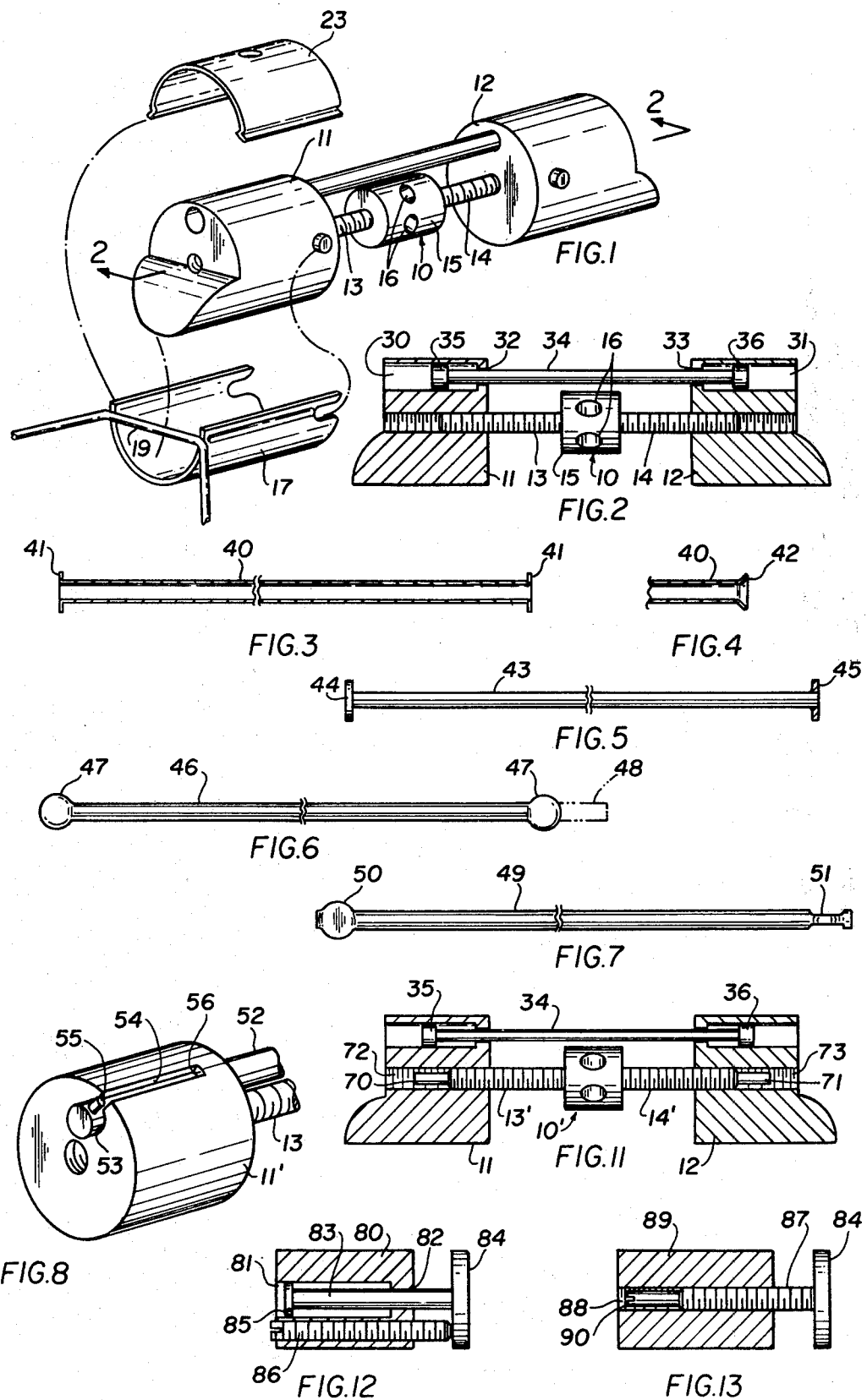

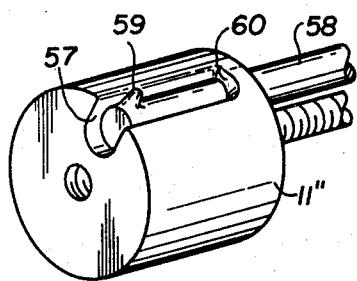
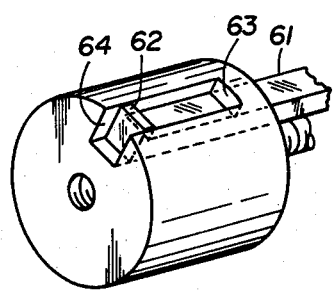
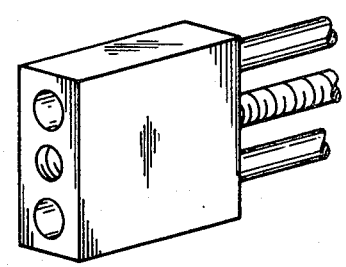
FIG.9   FIG.10   FIG.14
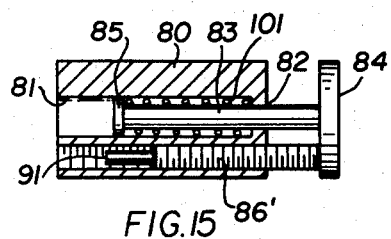
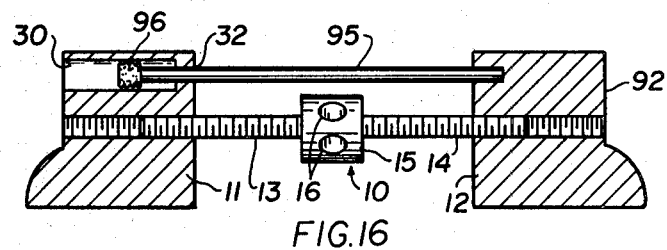
FIG.15   FIG.16
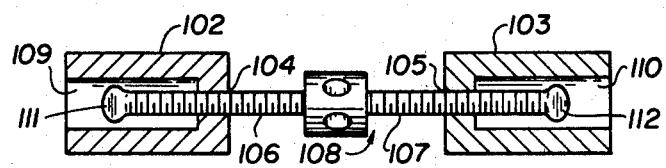
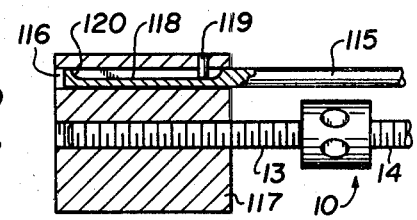
FIG.17   FIG.18
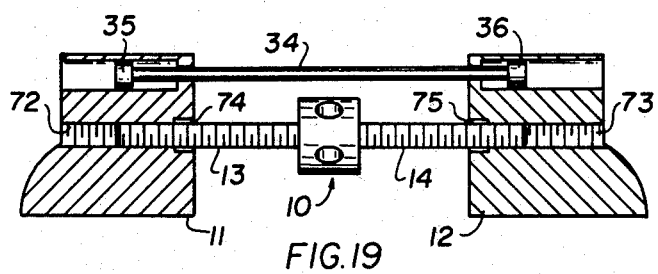
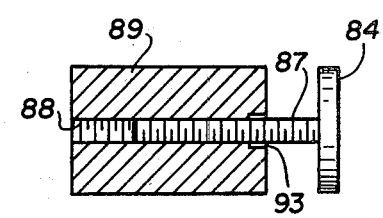
FIG.19   FIG.20
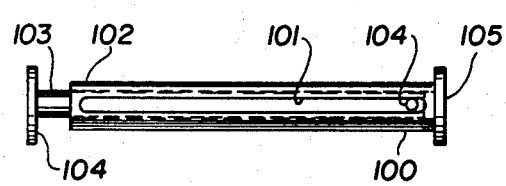
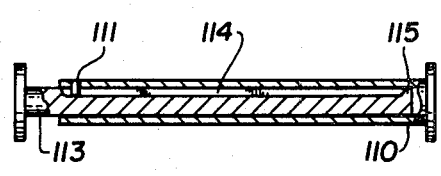
FIG.21   FIG.22

1

ORTHODONTIC BIASSING DEVICE WITH SCREW DISENGAGEMENT PREVENTING MEANS

This is a division of application Ser. No. 785,587 filed Apr. 7, 1977 now U.S. Pat. No. 4,200,979, issued May 6, 1980.

This invention relates to orthodontic devices, and more particularly to orthodontic biassing devices. The present invention is directed to improvements on biassing devices, such as those disclosed in my prior U.S. Pat. Nos. 3,832,778 and 3,921,294, as well as to other types of biassing devices.

In biassing devices having a screw-type actuation member, difficulties may arise when the screw actuation member is unthreaded to its maximum extent out of a threaded receiving element, or the like. At this point, there is a possibility that the screw will become disengaged and fall out of the remaining elements of the biassing device. This is undesirable and could cause a dangerous condition in the mouth of the patient.

The main object of the present invention is to provide orthodontic biassing devices which are screw actuated and which include means for preventing the screw from becoming disengaged from the remaining elements of the biassing device.

SUMMARY OF THE INVENTION

In accordance with the present invention, orthodontic biassing devices are provided with means for preventing the actuating screws from becoming disengaged from the body housings of the device. The retaining means may be either elongated members which are slidably retained in at least one body member, or may be provided on the screw members themselves, or even may be provided in the body housing means to cooperate with the screw members and/or the elongated retaining members.

Additionally, the present invention comprises a nested actuating screw arrangement for increasing the adjustment range of the biassing device, and a telescoping retaining means so that the biassing device may be used over a wider range. Still further, in accordance with the present invention, means is provided for preventing the threaded members from backing into the body housing under the reaction pressure of teeth, or the like.

BRIEF DESCRIPTION OF THE DRAWINGS

FIG. 1 is a perspective view showing the main portions of a typical biassing device in assembled form;

FIG. 2 is a cross-sectional view of the arrangement of FIG. 1 taken along the line 2—2 in FIG. 1;

FIG. 3 is a sectional view of a typical retaining member for use in the present invention;

FIG. 4 is a partial sectional view of a modified form of the retaining member of FIG. 3;

FIG. 5 illustrates another type of retaining member for use in the present invention;

FIG. 6 illustrates still another embodiment of a retaining device for use in the present invention;

FIG. 7 illustrates a further retaining device for use in the present invention;

FIG. 8 illustrates a modified arrangement of a biassing device according to the present invention;

FIG. 9 illustrates a still further modified arrangement of the biassing device of the present invention;

FIG. 10 illustrates still another embodiment of the present invention;

FIG. 11 illustrates a further embodiment of the present invention having a novel screw actuation member;

FIG. 12 illustrates an embodiment of the present invention applied to a different type of biassing device;

FIG. 13 illustrates a modified biassing device similar to that of FIG. 12 but utilizing a novel screw of the present invention;

FIG. 14 illustrates a still further embodiment of the present invention, similar to that of FIG. 1, but having rectangular end members and two retaining members;

FIG. 15 illustrates another embodiment of the present invention combining concepts of FIGS. 12 and 13;

FIG. 16 illustrates yet another embodiment of the present invention;

FIG. 17 illustrates another embodiment of the present invention;

FIG. 18 illustrates a further embodiment of the present invention;

FIGS. 19 and 20 illustrate a still further implementation of the present invention;

FIGS. 21 and 22 illustrate two embodiments of telescoping stabilizing and retaining devices according to the present invention;

DETAILED DESCRIPTION OF ILLUSTRATED EMBODIMENTS

Figure 23:
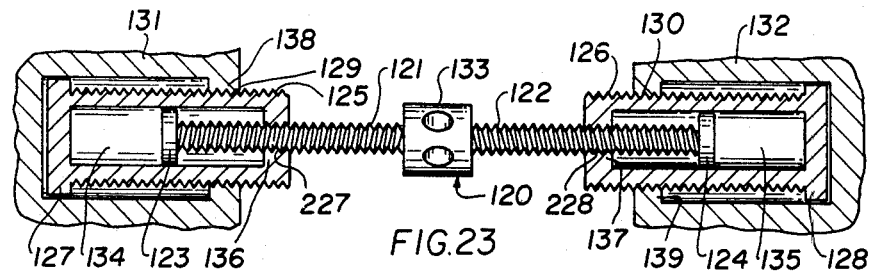
FIG. 23 illustrates a still further embodiment of the present invention.

The orthodontic devices of the present invention may be used similarly to those described in my prior U.S. Pat. Nos. 3,832,778 and 3,921,294, the contents of which are incorporated herein by reference. The present invention may also be used with other types of orthodontic biassing devices which do not specifically embody the inventive concepts of my said prior patents. Generally, the orthodontic devices of the present invention are adapted to be either directly connected to a tooth via wire members extending from the orthodontic devices, or to be embedded in acrylic devices which engage respective teeth, the orthodontic devices being utilized to vary the distance between the acrylic members and to thus spread apart teeth. The orthodontic expansion devices described herein can be easily adapted to operate as contraction devices within the scope of the present invention, as disclosed and claimed herein. Still further, the orthodontic devices of the present invention may be embedded in an acrylic device and be used to apply pressure to teeth relative to the acrylic device.

Referring to FIGS. 1 and 2, an expansion type orthodontic device includes two body members 11,12, each of which has an internal thread which respectively meshes with oppositely threaded screw portions 13,14 of an expansion screw 10. Positioned between the two screw portions 13,14 is a non-threaded spindle engaging portion 15 which is provided with radial holes 16 adapted to be engaged by a special tool or simply an elongated pin which may fit into the holes 16 so as to rotate the spindle. Rotation of the portion 15, which causes relative rotation between the screw portions 13,14 and the body members 11,12, either spreads the body members 11,12 apart or pulls them toward each other, depending upon the direction of rotation of the spindle engaging portion 15. In FIG. 1, the shell member 17 and cover 23 are shown only on the left-hand body member 11. A similar shell and cover may be provided for body member 12, for example as illustrated in my U.S. Pat. No. 3,921,294. The wire 19 attached to the shell 17 is attached to teeth by means of, for example, bands, or the like.

Each of the body members 11,12 has a bore 30,31 formed therein, each of which are in communication with respective smaller bores 32,33. A stabilizing rod-like member 34 passes through the smaller bores 32,33 and has enlarged end portions 35,36 which are slideable within the larger bores 30,31, respectively, but which do not pass through the smaller bores 32,33. As the screw 10 is unscrewed from the body members 11,12, and reaches toward the end of its travel, the enlarged portions 35,36 of rod member 34 will abut against the end walls of bores 30,31 adjacent bores 32,33, respectively, to prevent further spreading apart of the body members 11,12. Thus, the bar 34, with its enlarged ends 35,36, stabilizes the end body members 11,12 to prevent wobbling, and further limits the travel of the end body members 11,12 to prevent the screw 10 from becoming disengaged from end members 11,12.

As illustrated in FIG. 14, the end members 11,12 may be rectangular in shape and the expansion device may include two or more retaining and stabilizing rods 34, as desired. It should be clear that the end members may take any desired shape and that the rods 34 may also take any desired shape, such as rectangular, round, oval, etc. Further, the rods 34 may be hollow or solid, as will become apparent from the following.

FIG. 3 illustrates a hollow rod 40 having flanged ends 41 to act as the stop members as described in connection with FIGS. 1 and 2.

FIG. 4 illustrates a partial embodiment of a tubular or hollow rod 40 having gently flared ends 42 which may be formed, for example, by ramming a tapered member in the end of a tube.

FIG. 5 illustrates a rod 43, which may be solid or hollow, and having an upset head 44 at the left end thereof and a brazed or welded flange washer 45 at the right end thereof.

FIG. 6 illustrates a further rod 46 according to the present invention having ends drawn into a restricting ball 47, for example by arc welding. In FIG. 6, at the right end thereof, the portion 48 which is drawn into the ball 47 is shown in phantom lines.

FIG. 7 illustrates a rod 49 which has crimped ends 50,51. The ends 50 and 51 are shown perpendicular to each other so as to clearly illustrate the crimps. The crimped ends 50,51 may be formed by conventional means, such as hammering, squeezing, or the like.

FIG. 8 partially illustrates a further embodiment of the present invention wherein a body member 11' has a screw 13, which is part of a screw 10, threaded therein and a stabilizing rod 52 slideably mounted in a bore 53 in the end member 11'. The end member 11' further has a slotted portion 54 in communication with the bore 53 through which a pin 55 attached to the rod 52 passes. FIG. 8 illustrates only the left body member 11'. The right body member may be similar to the left body member or may be different, as desired. As the body members are expanded away from each other, the pin 55 will eventually abut against the wall 56 or slot 54, thereby preventing further movement of the body member 11' relative to the screw 13, to stabilize the device and to prevent disengagement of the screw 13 from the body member 11'.

FIG. 9 partially illustrates a further embodiment of the present invention wherein a body member 11" has a groove 57 formed therein, a stabilizing bar 58 being slideably mounted in the grove. The stabilizing bar 58 has a "pinched up" end 59 which abuts against the end wall 60 of the groove 57 to limit movement of the body member 11" relative to the bar 58.

FIG. 10 partially illustrates a further embodiment of the invention similar to that of FIG. 9 except that the groove 64 is generally rectangular in cross-section and a generally rectangular rod 61 is slideably mounted therein. The rod 61 has an upstanding portion 62 which abuts against an end surface 63 of the groove 64 to limit movement of the end member relative to the rod 61.

FIG. 11 illustrates another embodiment of the invention similar to that of FIGS. 1 and 2, but wherein the screw members 13',14', have non-threaded end portions 70,71 which are of reduced diameter relative to the maximum external diameter of the screws. As the screw device 10' is unthreaded from the end members 11,12 to its maximum extent, the end portion 70 and 71 will remain in the threaded bores 72,73, respectively, thereby preventing the screw device 10' from becoming disengaged from the end members 11,12. The modified screw device 10' can be used by itself in the end members 11,12, or may be used in conjunction with rod member 34 having enlarged ends 35,36, as illustrated in FIG. 11, to provide still further stability and protection against disengagement of the screw device 10' from the end members 11,12. As should also be apparent, more than one rod member 34 may be used in conjunction with modified screw device 10'.

FIG. 12 illustrates another type of orthodontic device with which the present invention is useful. A body member 80 is connectable to, for example, a tooth, by means of wires, bands, or the like, or is embedded in an acrylic appliance. The body member 80 has first and second bores 81,82 formed therein, through which a bar-type member 83 is slideable. The bar member 83 has a pushing member 84 at the end thereof for applying an orthodontic force. At the opposite end of bar 83 is an enlarged portion 85 which passes through first bore 81, but does not pass through second bore 82. Thus, the enlarged portion 85 will limit the movement of the bar 83 relative to the body member 80. By turning the screw 86, which is threadably engaged in a threaded bore of the body 80, the bar 83 and its pushing member 84 are moved to the right relative to the body member 80 as seen in FIG. 12. The enlarged end portion on the rod 83 prevents disengagement of the screw 86 from the body member 80.

FIG. 13 illustrates a further embodiment of the present invention wherein the pushing member 84 is connected to a threaded member 87 which is threadably engaged in a threaded bore 88 of a body member 89. The screw 87 has a reduced diameter non-threaded portion 90 at the end thereof. As the screw is unthreaded from the body member 89 to its maximum extent, the reduced diameter portion 90 will remain in the threaded bore 88 to prevent disengagement of the screw 87 and pushing member 84 from the body member 89. A rotatable joint may be provided between member 84 and screw portion 87 so that the screw portion 87 may rotate relative to the member 84.

As should be apparent, the concepts of FIGS. 12 and 13 could be combined by providing a reduced diameter non-threaded portion 91 at the left end of the screw 86', as shown in FIG. 15. Thus, the embodiment of FIGS. 12, 13 and 15 provide not only stability of the pushing member 84, but also prevent disengagement of the pushing member 84 and its associated rod, either threaded or unthreaded from the body member 80,89. A coil spring 101 is optionally provided as shown in FIG. 15 in order to bias pushing member 84 against screw 86' to facilitate insertion of the device into the mouth of a patient.

While it is preferably to have the stabilizing and disengagement preventing rod 34 freely slideable in both end body members 11,12 as shown in FIGS. 1 and 2, it is possible to provide one or more stabilizing rods which are fixed in one of the end body members, and which is slideable in the other of the body members, the slideable end having an enlarged end portion as shown in FIGS. 1 and 2. Such a modified form of the invention is shown by way of example in FIG. 16.

Referring to FIG. 16, the body member 11 and the screw device 10 are similar to the corresponding elements in FIGS. 1 and 2, and corresponding reference numerals are used. The body member 92 at the right side of the embodiment of FIG. 16 has a stabilizing and disengagement prevention rod 95 fixed thereto. The free end of the bar 95 is slideable in the bores 30,32 of body member 11, said free end of the bar 95 being roughened or otherwise formed at 96 so as not to pass through the smaller diameter bore 32. It should be clear, however, that the free end 96 of bar 95 may be otherwise formed such as, for example, shown in the other figures of the drawings. As seen in FIG. 16, when the screw device 10 is fully threaded in both of the body members 11,92, due to the fact that the bar 95 is fixedly mounted in one of the body members 92, the free end 96 will extend outwardly of the body member 11. In some instances, an obstruction in the mouth of a patient could prevent use of the embodiment of FIG. 16 wherein the bar member 95 extends outwardly (that is, to the left) of the body member 11 as seen in FIG. 16. This is due to the fact that relative movement between the bar 95 and the end body member 11 will be twice the relative movement between the screw portion 13 and the body member 11. This is due to the fact that the bar 95 is fixed at one end to body member 92. In order to prevent the bar 95 from projecting outwardly of the body member 11, a screw 10 having a smaller length must be used.

As should be apparent from the above, the embodiment of the present invention wherein both ends of the bar 34, for example as shown in FIG. 2, are freely slidable in the respective body members 11,12, has the advantage that full travel of the body members 11,12 relative to the screw member 10 can be provided without having either end of the bar 34 project outwardly of the outer extreme ends of body members 11,12. This "floating" movement of the retaining and stabilizing bar 34 relative to the body members 11,12 is therefore advantageous.

FIG. 17 illustrates another embodiment of the invention comprising body members 102,103 having small diameter threaded bores 104,105, respectively, which threadably engage oppositely threaded screw portions 106,107, respectively, of an expansion screw 108. Threaded bores 104,105 are in communication with larger diameter bores 109,110, respectively, of body members 102,103. The ends of the screw portions 106,107 are crimped or otherwise deformed or enlarged so that they freely pass through bores 109,110 but do not pass through threaded bores 104,105. Body members 102,103 are attached to teeth by means of wires, or the like, in the same manner as the body members of FIGS. 1 and 2. As the threaded screw member 108 is unthreaded from body members 102,103, when the screw portions 106,107 reach the end of their engagement with threaded bores 104,105, the crimped end portions 111,112 will not pass through threaded bores 104,105, thus limiting movement of the threaded screw 108 relative to the body members 102, 103. This prevents the screw member 108 from becoming disengaged from the body members and falling into the mouth. Stabilizing rods, such as rod 34 or the like could be used in conjunction with the expansion screw 108 shown in FIG. 17, as should be apparent.

It should be clear that the embodiment of FIG. 13 could be modified to provide an enlarged end on screw 87 in place of the reduced diameter portion, and to provide an enlarged bore in communication with a smaller threaded bore as shown, for example in FIG. 17, to limit unthreading of screw 87 from body member 89.

FIG. 18 illustrates a further embodiment of the invention wherein a stabilizing and retaining rod 115 is slideably mounted in a bore 116 of a body member 117. The rod 115 has an elongated depression 118 therein and the body member 117 has a pin or set screw 119 therein so as to intrude into the void presented by the depression 118. As the rod 115 moves out of the body member 117 upon actuation of the screw member 10, the pin or set screw 119 will abut against the end wall 120 of depression 118 so as to limit the travel of the rod 115 relative to the body member 117, thereby preventing screw member 10 from becoming disengaged from body member 117. The right-hand portion of the device shown in FIG. 18 may be identical to the illustrated left end portion, or may be modified as, for example, one of the previously described arrangements.

FIG. 19 illustrates a modified form of the arrangement shown in FIG. 11. In the embodiment of FIG. 19, respective bores 72,73 of body members 11,12 have enlarged or unthreaded mouth portions 74,75. As the expansion screw 10 is unthreaded from the body members 11,12, when the screw portions 13,14 reach the unthreaded or enlarged mouth portion 74,75, further expansion of body members 11,12 ceases. The unthreaded portions 74,75 act as retainers to prevent the expansion screw 10 from becoming disengaged from the body members 11,12. The enlarged openings 74,75 may be used in conjunction with one or more stabilizing rods or bars 34, as shown in FIG. 19 or in any of the other figures, or may be used without such stabilizing rods or bars, as should be apparent.

FIG. 20 is a modified form of the invention using the concept illustrated in FIG. 19. FIG. 20, which is similar to the arrangement of FIG. 13, utilizes an enlarged, non-threaded portion 93 at the opening or mouth of the threaded bore 88 so that as the screw member 87 is unthreaded from the body member 89, the displacement between the screw member 87 and the body member 89 ceases when the screw member reaches the unthreaded portion 93, thereby preventing the screw member from becoming disengaged from the body member 89. Since the device of FIG. 20 operates as an expansion device, and there is always pressure against member 84 tending to push the threaded member 87 back into the threaded bore 88 of the body member 89, there is very little danger that the threaded member 87 will become disengaged from the body member 89. Is should be clear that the arrangement of FIG. 20 may be utilized in arrangements such as those shown in FIGS. 12 and 15. Also, stabilizing bars, or the like, could be used with this embodiment.

With respect to FIGS. 19 and 20, it should be clear that the precise dimensions and arrangements of the openings 74,75 and 93 may be varied within rather wide limits. The length of the opening in the axial direction of the threaded bores may also be varied. Still further, the portions 74,75 and 93 need not be unthreaded, but may be dimensioned or configured such that the respective threaded members will not move relative to the respective body members when they are turned in the portions 74,75 and 93.

FIGS. 21 and 22 illustrate telescoping retaining and stabilizing bars for use in the present invention. Telescoping retaining and stabilizing bars are particularly useful in, for example, the embodiment of FIG. 16 wherein one end of the bar is fixed to a body member. The arrangements of FIGS. 21 and 22 may have one end fixed in a body member, such as shown in FIG. 16.

Referring to FIG. 21, the telescoping member comprises an outer tubular member 100 having a slot 101 along the axial direction thereof. The slot is closed at the remote end 102 of the outer tubular member 100. Slideably mounted within the outer tubular member 100 is an inner rod-like member 103 which may be solid or tubular, and which has an enlarged portion 104 at the end thereof. The enlarged portion may be crimped, deformed, roughened or any of the other particular configurations illustrated in the drawings. The outer tubular member 100 may have a similar enlarged end portion 105, or may be straight for embedding same in a body member, such as body member 14 of FIG. 16. The inner rod 103 has a pin or the like protruding therefrom which engages in the slot 101. As can be seen from FIG. 21, when the inner rod 103 is withdrawn to its maximum extent from the outer tubular member 101, the pin 104 will abut the end portion 102 of the outer tubular member 100 to prevent further displacement between the inner rod and outer tubular member.

FIG. 22 shows a modified arrangement wherein an outer tubular member 110 has a pin 111 mounted at the end thereof and which extends to the interior of the outer tubular member 110. Slideably mounted within the outer tubular member 110 is an inner rod, or the like 113 which has a longitudinal groove 114 formed therein. As the inner rod 113 is withdrawn from the outer tubular member 110, the pin 111 will eventually abut against the end portion 115 of the inner rod 113 to prevent further displacement of the inner rod 113 relative to the outer tubular member 110.

The embodiments of FIGS. 21 and 22 are exemplary and it should be clear that various modifications and alterations can be made to still provide telescoping guide and retaining bars for the biassing devices of the present invention.

FIG. 23 illustrates a further embodiment of the present invention utilizing a nesting expansion screw arrangement. This provides increased expansion lengths while reducing the intervals between changing of expansion screws. As shown in FIG. 23, the expansion screw 120 comprises inner screw members 121,122 which are oppositely threaded. The oppositely threaded screws 121,122 have respective abutment members 123,124 at the ends thereof, the functions of which will become apparent from the following discussion. The expansion screw 120 further comprises outer screw members 125,126 which respectively threadably engage inner screws 121,122 at the threaded portions 227,228 thereof. The outer surfaces of outer screws 125,126 are oppositely threaded with respect to each other. The outer screws 125,126 have abutment members 127,128, respectively, at the ends thereof. The outer threads of the outer screws 125,126 threadably engage threaded portions 129,130 of respective body members 131,132. The body members 131,132 are only partially shown, it being clear that stabilizing and retaining bars, such as those shown in any of the previously described embodiments, could be used in conjunction therewith. In the illustrated embodiment, the threads of the various screw members have the same pitch. However, different pitches could be used for the inner and outer screws, if desired.

In operation, as the spindle engaging portion 133 of the expansion screw 120 is rotated by the user, either the inner or outer screws will also rotate relative to the respective body members 131,132. It is not relevant whether the inner or outer screws rotate at this time. By way of explanation, assuming that the inner screws rotate relative to the outer screws, as the inner screw reaches the end of its threaded engagement with the portion 127,128 of the outer screw. The abutment members 123,124, which are slideable within the hollowed out portions 134, 135 of the respective outer screws 125,126, will abut against the inner walls 136,137 of the outer screws to prevent further relative rotation between the inner and outer screws. At this time, further rotation of the spindle engaging portion 133 will cause the outer screws to rotate relative to the respective body members. When the outer screws reach the end of their threaded engagement with the respective body members 131,132, the abutment portions thereof will abut against respective inner wall portions 138, 139 of the respective body members 131,132. At this point, the spindle engaging portion 133 can no longer be rotated, and the expansion screw is prevented from becoming disengaged from the respective body members.

It should be clear that the embodiment of FIG. 23 may be modified. For example, the enlarged end portions 123, 124, 127, 128 are shown only by way of example. Other members or means which prevent relative rotation between the respective screws and between the outer screw and the body member may be used, or the screw ends could be peened over. Also, it is possible that when the spindle engaging portion 133 is initially rotated, the outer screw will rotate relative to the body member in the first instance, and then the inner screw will rotate relative to the outer screw. In this mode of operation, the desired result is still achieved in that disengagement of the expansion screw 120 from the body members 131,132 is prevented, while providing a full range of adjustment of the biassing device. As mentioned above, the body members 131,132 are only partially shown—they clearly may take any desired form, such as round, rectangular, oval, or the like, and are non-rotatably mounted to teeth or other orthodontic members in a mouth of a patient.

Figure 24:
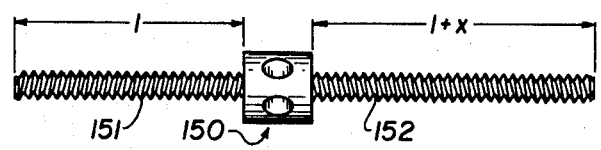
FIG. 24 illustrates yet another embodiment of the present invention.

FIG. 24 illustrates a further means according to the present invention for preventing an expansion screw from becoming disengaged from the body members to which it is threadably engaged. Referring to FIG. 24, an expansion screw 150 has left and right screw members 151,152 which are oppositely threaded with respect to each other. Screw member 151 is shorter than member 152 by an amount "x". As the expansion screw 150 is threaded out from respective body members, such as body members 11,12 of FIGS. 1 and 2, when the shorter portion 151 becomes threadably disengaged from body member 11, a portion "x" of screw member 152 will remain threaded in the other body member, for example body member 12. This will prevent the expansion screw 150 from becoming completely disengaged from the expansion device and falling into the mouth of a patient. When the screw member 151 becomes threadably disengaged from its body member 11, it will usually become somewhat displaced therefrom so that the user will readily discover that the expansion screw 150 has reached its maximum travel. The length "x" by which the longer screw member 152 is longer than the screw member 151 may be varied, as suits the particular requirement. However, a value of "x" of about 2-4 mm is suitable for general application.

Figure 25:
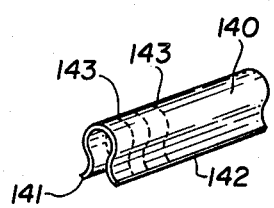
FIGS. 25 and 26 illustrate a retaining member in accordance with the present invention.

During orthodontic treatment, it sometimes becomes desirable to cease further actuation of the expansion screw device and to use it as a holding member in the mouth. However, since the teeth will tend to collapse back to their original positions, the teeth exert a force on the expansion device which tends to cause the screws to back into the body members. This is clearly disadvantageous. It is desired at this point to lock the screws relative to the body members to prevent the screws from backing into the body members due to the pressure of the tendency of the teeth to return to their original positions. FIG. 25 illustrates a means according to the present invention for preventing the back pressure of the teeth from causing the screws to back into the respective body members when it is no longer desired to impart further expansion.

Figure 26:
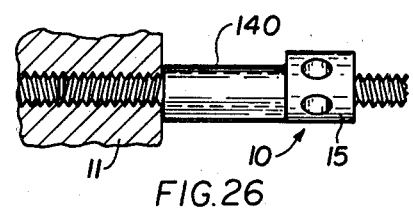

Referring to FIG. 25, a means for preventing back pressure from backing the screws into the body members comprises an elongated generally U-shaped member which is adapted to be snapped over a screw to retain it in position relative to the body member. The sleeve 140 of FIG. 25 is preferably made of a material which permits flexing thereof as the ends 141,142 are pressed over an expansion screw and snapped into place on the expansion screw. The ends 141,142 are flared outwardly to facilitate snapping the member 140 over an expansion screw. The member 140 may be made of spring metal, relatively rigid plastic material, or the like. When it is made of plastic material, it must have sufficient strength in its longitudinal direction to prevent the backing in pressure of the teeth from causing the screw to back into the body member. The member 140 may have weakened areas 143 at which it may be snapped off to adjust same to the desired length. Alternatively, the length of the member 140 may be varied by snipping same off with a cutting implement, such as scissors, diagonal cutters, or the like. FIG. 26 illustrates a member 140 snapped into place over a screw of the expansion device and interposed between the spindle engaging portion 15 and a body member 11. If desired, to improve reliability, a similar member 140 may be installed on the other side of the spindle engaging member 15 and the other body member (not shown). Still further, if desired, the member 140 may be made large enough to snap over the spindle engaging member 15 and to span the distance between the body members (such as body members 11,12 of FIG. 2) to achieve substantially the same result.

Figure 27:
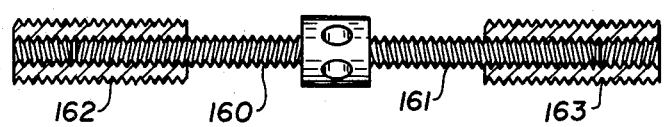
FIG. 27 illustrates a double screw arrangement for use in the present invention.

FIG. 27 illustrates a nested screw arrangement comprised of inner oppositely threaded screws 160,161 which are threadably engaged in outer oppositely threaded screws 162,163. The screw of FIG. 27 may be used in place of the expansion screws of any of the embodiments of the invention as well as in conventional biassing devices.

Figure 28:
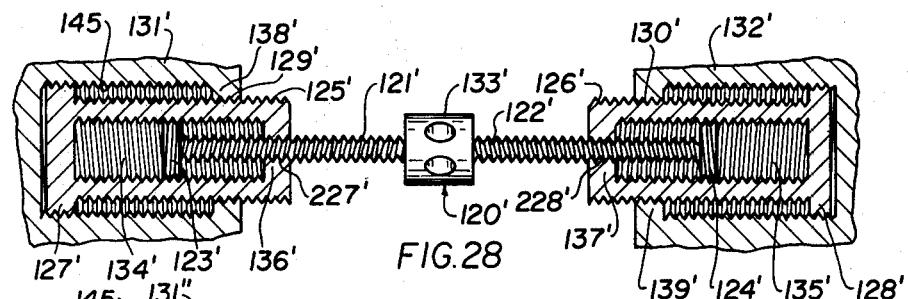
FIGS. 28 and 29 illustrate further double screw arrangements according to the present invention.

FIG. 28 illustrates a further nested screw arrangement similar to that of FIG. 23, but wherein the abutment portions 123',124', 127', 128' have their outer surfaces threaded and wherein the corresponding enlarged inner bores of the housing and outer screw have their inner surfaces threaded so as to threadably engage the threaded abutment members 123', 124', 127', 128'. The arrangement of FIG. 28 has the advantage that the threading of the abutment members and of the inner surfaces of the enlarged bores provides a stronger and more rigid expansion device. Operation of the device of FIG. 28 is substantially identical with that of FIG. 23.

Figure 29:
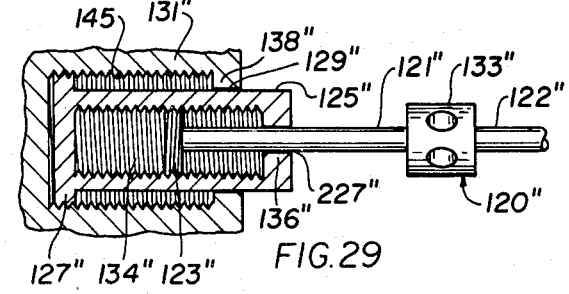

FIG. 29 illustrates a further nested screw arrangement according to the present invention wherein the outer housing 131 has a large bore 145 which is internally threaded and a smaller bore 129" which is not threaded. An abutment surface 138" is formed between the outer bore 145 and the inner bore 129". An outer member 125" has an abutment member 127" at the end thereof which is also threaded so as to threadably engage the inner threaded surface of large bore 145. The inner member 121" is unthreaded and has a threaded abutment member 123" at the end thereof which threadably engages the threaded inner surface of the large bore 134" of the outer member 125". Outer member 125" has a smaller bore 227" at the mouth thereof which defines an abutment surface 136" which abuttingly engages abutment member 123". The surfaces 227" and 129" act as bearing and support members for the elongated members 121" and 125" respectively. The arrangement of FIG. 29 operates substantially similarly to that of FIG. 23 and a detailed explanation of the operation thereof is not given herein.

In FIGS. 27 and 28, only the left-hand portion of the nested screw arrangement is shown. The right-hand portion, however, is identical with the left-hand portions except that the various threaded members are oppositely threaded with respect to the left and right-hand members to provide proper expansion upon turning of the spindle engaging member of the nested screw arrangements.

In any of the nested screw arrangements illustrated herein, the outer screw member may have a finer thread (such as, for example, an 8-64 thread) than the inner screw member which may have, for example, a 3-48 thread. Since the outer screw member will have a finer thread, turning of the spindle engagement member will cause the outer or heavier screw to initially turn to provide the initial expansion force. In orthodontic operations, the initial expansion force is generally the highest and creates the most back pressure on the expansion device. Therefore, in some instances it is desired that the outer, heavier screw member rotate initially to provide this initial force, which effect can be obtained by making the outer thread finer than the inner thread. Such an arrangement wherein the threads have different pitch is particularly advantageous in a nested screw arrangement wherein only, for example, the outer screw member has a stop means thereon for preventing rotating thereof relative to the body housing when a predetermined engagement position is reached. At this point, since relative rotation between the body housing and the outer screw is prevented, the inner screw will of necessity rotate when the spindle engaging member is rotated. In instances where there is no danger of the expansion screw becoming disengaged from the body member, for example when the degree of expansion is known beforehand, such an arrangement using different pitches for the inner and outer screws and using a rotating prevention means only on the outer screw member is advantageous in that it provides a more economical to manufacture device. In particular, with respect to the arrangement of FIG. 27, the concept of providing a finer pitch on the outer screw member and a stop means therefor, in combination with a more coarse pitch on the inner screw member is advantageous. Still further, the inner screw member in the embodiment of FIG. 27 may be the unequal length screw member of FIG. 24, to further prevent disengagement of the expansion screw from the rest of the device.

The embodiment of FIG. 17 may, for example, be modified along the lines of the concepts illustrated in FIGS. 28 and 29. A modification along the lines of FIG. 28 would comprise replacing the flattened portion 111,112 with enlarged cylindrical abutment members which are externally threaded, and by threading the internal surfaces of boxes 109,110 to engage the threaded abutment portions which replace the portions 111,112. A modification of FIG. 17 along the lines of FIG. 29 would comprise replacing the end portions 111,112 with cylindrical abutment portions having a threaded outer periphery, and by threading the inner surface of enlarged bores 109,110. The remainder of the screw portion 106,107 would be unthreaded, as would the inner surfaces of the smaller bores 104,105. The elongated unthreaded portions would thus be supported in the bearing formed by the unthreaded surfaces of the smaller bores 104, 105. The enlarged threaded abutment members at the ends of the elongated unthreaded members would abut against the inner surface of the wall which defines the transition between enlarged opening 109,110 and smaller openings 104,105, respectively.

The arrangement of FIG. 27 is utilizable in conventional orthodontic biassing devices, assuming that the threaded bore thereof is of sufficient size to receive the elongated threaded members 162,163. When utilizing the arrangement of FIG. 27 in a conventional biassing device, it is preferable that the inner screw members 160,161 have a finer thread than the outer screw members 162,163. Moreover, it is preferable that the inner screw members 160,161 have abutment means at the end thereof, similar to abutment means 123 shown in FIG. 23, and that the outer screw members 162,163 have, for example, an enlarged bore 134 and smaller threaded bore 227 so as to cooperate with the abutment member 123. This type of modified arrangement will insure that the inner screw rotate initially (since it has a finer threaded) and when the inner screw reaches the end of its travel (such as when the abutment member 123 abuts the wall 136 of the outer screw member), the outer screws 162, 163 will be caused to rotate upon further turning of the spindle engaging member. If desired, the outer screw members 162,163 may be then made of unequal length, for example as shown in FIG. 24, to further prevent disengagement of the threaded members from the body housings, or the like.

While the invention has been described above with respect to specific embodiments, it should be clear that various modifications and alterations could be made within the scope of the invention as defined in the appended claims. For example, in any of the embodiments, more than one stabilizing and retaining rod of the present invention could be used to provide improved stability of the device. Moreover, the particular design of the end members 11,12, 80,89 can be varied, the particular designs shown in the drawings being merely exemplary. Moreover, the biassing devices may be used in fixed appliances in the mouth, as well as removable. They may be mounted via extension arms (i.e., metal arms) or may be embedded in plastic members. The various features of the invention may be combined in any combination.

I claim:

1. An orthodontic biassing device comprising:

two oppositely disposed body members adapted to engage one or more teeth and to be spaced from each other, each of said body members having a threaded bore directly formed therein, said threaded bores being oppositely threaded;

an elongated threaded member having oppositely threaded end portions which are respectively threadably engaged in the threaded bores of said body members to selectively expand or contract the spacing between said body members;

first abutment means directly formed on at least one of said body members; and retaining means coupled to and being movable relative to said at least one of said body members for abuttingly engaging with said first abutment means on said at least one of said body members for positively preventing relative movement between said elongated threaded member and said body members when the spacing between said body members is expanded to a predetermined spacing, thereby preventing disengagement of said elongated threaded member from said body members.

2. A biassing device according to claim 1 wherein said retaining means comprises means slideably engaged in said at least one body member for selectively and abuttingly engaging said first abutment means of said at least one body member.

3. A biassing device according to claim 2 wherein said at least one body member has a further bore therein, said further bore having a smaller cross-sectional portion and a larger cross-sectional portion in communication with said smaller cross-sectional portion, and wherein said retaining means comprises at least one elongated member slideably received in said further bore, said at least one elongated member having second abutment means at an end portion thereof which is possible through said larger cross-sectional portion of said further bore but which is not passable through said smaller cross-sectional portion of said further bore.

4. A biassing device according to claim 3 wherein said second abutment means at the end portion of said at least one elongated member comprises an enlarged portion.

5. A biassing device according to claim 3 wherein said second abutment means at the end portion of said at least one elongated member comprises an outwardly bulged portion.

6. A biassing device according to claim 3 wherein said second abutment means at the end portion of said at least one elongated member comprises extending means extending from a surface of said elongated member generally perpendicular to the longitudinal direction thereof.

7. A biassing device according to claim 3 wherein each of said body members has said further bore therein, and said at least one elongated member of said retaining means is slideably engaged at least in the smaller cross-sectional portions of said further bores and has second abutment means at both ends thereof which are passable through said larger cross-sectional portions of said further bores, but which are not passable through said smaller cross-sectional portions of said further bores.

8. A biassing device according to claim 3 wherein said at least one elongated member is fixedly connected to the other of said body members.

9. A biassing device according to claim 3 wherein said threaded bore of said at least one body member extends only partially through said at least one body member and communicates with a further bore which has a smaller internal dimension than said threaded bore, and said retaining means comprises an outwardly bulged portion at the end portion of said threaded member which threadably engages said threaded bore of said at least one body member, said outwardly bulged portion being threadably passable through said threaded bore and being non-passable through said smaller bore.

10. A biassing device according to claim 2 wherein said at least one body member has at least one further bore therein, and wherein said retaining means comprises at least one elongated member slideably received in said at least one further bore, said elongated member having second abutment means for engaging said first abutment means of said at least one body member.

11. A biassing device according to claim 10 wherein said at least one body member comprises a slot therein which is in communication with a portion of said at least one further bore, said slot at least partially defining said first abutment means, and wherein said second abutment means comprises an extending member from said elongated member which is slideable in said slot and which is not passable through the portion of said at least one further bore which is not in communication with said slot, said first and second abutment means being selectively abuttingly engageable with each other to prevent said relative movement.

12. A biassing device according to claim 10 wherein said elongated member comprises an elongated, axially directed depression in a portion thereof except for the end thereof, the end of said elongated member defining said second abutment means, and said first abutment means of said at least one body member is engageable in said depression for abutting against said end of said elongated member for preventing said relative movement.

13. A biassing device according to claim 2 wherein said retaining means comprises a telescoping elongated retaining means.

14. A biassing device according to claim 13 wherein said telescoping elongated retaining means comprises a first elongated member having a hollow portion, and a second elongated member slideably received in said hollow portion of said first elongated member, and means coupled to said members for preventing said second elongated member from sliding completely out of engagement with said first member.

15. A biassing device according to claim 14 wherein said first member has an elongated slot therein, and said second member has a pin-like member protruding therefrom and engageable in said elongated slot, said elongated slot having a termination point which is engageable with said pin-like member to prevent disengagement of said first and second members.

16. A biassing device according to claim 14 wherein said second member has an axial groove therein which terminates short of the end of said second member, and said first member has a pin-like member therein which extends into said hollow portion and engages in said groove, said pin-like member engaging an end wall of said groove proximate the end of said second member to prevent disengagement of said first and second members.

17. A biassing device according to claim 1 wherein both of said body members have respective first abutment means, and said retaining means includes means for selectively and abuttingly engaging with said first abutment means of both of said body members for preventing disengagement of said elongated threaded member from said body members.

18. A biassing device according to claim 1 wherein said retaining means comprises second abutment means coupled to said elongated threaded member abutting said first abutment means for preventing unthreading of said elongated threaded member from said at least one body member.

19. A biassing device according to claim 18 wherein said second abutment means comprises an enlarged end portion of said threaded member.

20. A biassing device according to claim 18 wherein said second abutment means comprises an outwardly bulged end portion of said threaded member.

21. A biassing device according to claim 18 wherein said threaded bore of said at least one body member extends only partially through said at least one body member and communicates with a further bore which has a larger internal dimension than said threaded bore, the transition between said threaded bore and said further bore comprising said first abutment means, and said second abutment means of said retaining means comprises an enlarged portion at the end portion of said threaded member which engages said threaded bore of said at least one body member, said enlarged portion being passable through said further larger internal bore and being non-passable through said threaded bore.

22. A biassing device according to claim 21 wherein said further bore has an internal thread thereon and said enlarged portion has an external thread thereon which threadably engages the internal thread of said larger bore.

23. A biassing device according to claim 18 wherein said threaded bore of said at least one body member extends only partially through said at least one body member and communicates with a further bore which has a larger internal dimension than said threaded bore, the transition between said threaded bore and said further bore comprising said first abutment means, and said second abutment means of said retaining means comprises an outwardly bulged portion at the end portion of said threaded member which engages said threaded bore of said at least one body member, said outwardly bulged portion being passable through said further internal bore and being non-passable through said threaded bore.

24. A biassing device according to claim 23 wherein said further bore has an internal thread thereon and said outwardly bulged portion is threaded to threadably engage the threads of said larger bore.

25. A biassing device according to claim 18 wherein said threaded bore of said at least one body member extends only partially through said at least one body member and communicates with a further bore which has a smaller internal dimension than said threaded bore, and said retaining means comprises an enlarged threaded portion at the end portion of said elongated threaded member which engages said threaded bore of said at least one body member, said enlarged portion being passable through said threaded bore and being non-passable through said smaller bore.

26. An orthodontic biassing device comprising:
two oppositely disposed, spaced body members adapted to engage one or more teeth, each of said body members having a threaded bore directly formed therein, said threaded bores being oppositely threaded;
an elongated threaded member having oppositely threaded end portions which are respectively threadable in the threaded bores of said body members to selectively expand or contract the spacing between said body members;
at least one of said body members having a further bore directly formed therein and stop means integral with said at least one body member and being in communication with said further bore; and
a stabilizing and retaining bar slideably mounted in said further bore of said at least one body member and having means thereon for engaging said stop means to restrict relative movement between said bar and said at least one body member.

27. An orthodontic biassing device according to claim 26 wherein said stop means in communication with said bore comprises a second bore of smaller diameter than said further bore, said second bore being in communication with said further bore.

28. An orthodontic biassing device according to claim 26 wherein said stop means comprises a wall of said at least one body member adjacent said bore.

29. An orthodontic biassing device according to claim 26 wherein both of said body members have a further bore therein and respective stop means in communication with said further bores, said stabilizing and retaining bar being slidably mounted in said further bores of each of said body members and having means thereon for engaging said respective stop means of said body members to restrict relative movement between said bar and said body members.

30. An orthodontic biassing device according to claim 29 wherein said stabilizing and retaining bar comprises abutment means for engaging said stop means of said body members.

31. An orthodontic biassing device according to claim 30 wherein said abutment means comprises an enlarged portion at the end portion of at least one end of said bar.

32. An orthodontic biassing device according to claim 30 wherein said abutment means comprises an outwardly extending portion at the end portion of at least one end of said bar.

33. An orthodontic biassing device comprising:
two oppositely disposed, spaced apart body members adapted to engage one or more teeth, each of said body members having a threaded bore formed directly therein, said threaded bores being oppositely threaded;
an elongated threaded member having oppositely threaded end portions which are respectively threadable in the threaded bores of said body members to selectively expand or contract the spacing between said body members; and
retaining means on said elongated threaded member and cooperating with said body members for preventing said elongated threaded member from becoming disengaged from said body members when unthreaded to its maximum extent from said body members, said preventing means comprising reduced diameter end portions of said elongated threaded member remaining in said threaded bores of said body member upon unthreading of said elongated threaded member to its maximum extent from said body members.

34. An orthodontic biassing device comprising:
a single body member having a threaded bore directly formed therein and first abutment means directly formed thereon;
an elongated threaded member threadably engaged in said threaded bore of said body member;
means coupled to said threaded member for applying an orthodontic force to at least one tooth; and
retaining means coupled to and being movable relative to said single body member for abuttingly engaging with said first abutment means of said body member for positively preventing relative movement between said threaded member and said body member when said threaded member is unthreaded a predetermined amount from said threaded bore of said body member, thereby preventing disengagement of at least one of said threaded member and force applying means from said body member.

35. A biassing device according to claim 34 wherein said retaining means comprises means slideably engaged in said body member for selectively and abuttingly engaging said first abutment means of said body member.

36. A biassing device according to claim 35 wherein said force applying means is coupled to said means slideably engaged in said body member.

37. A biassing device according to claim 36 wherein said body member has a further bore therein, said further bore having a smaller cross-sectional portion and a larger cross-sectional portion in communication with said smaller cross-sectional portion, and wherein said slideably engaged means comprises at least one elongated member slideably received in said further bore, said at least one elongated member having second abutment means at an end portion thereof which is passable through said larger cross-sectional portion of said further bore but which is not passable through said smaller cross-sectional portion of said further bore.

38. A biassing device according to claim 37 wherein said second abutment means at the end portion of said at least one elongated member comprises an enlarged portion.

39. A biassing device according to claim 37 wherein said second abutment means at the end portion of said at least one elongated member comprises an outwardly bulged portion.

40. A biassing device according to claim 37 wherein said second abutment means at the end portion of said at least one elongated member comprises extending means extending from a surface of said elongated member generally perpendicular to the longitudinal direction thereof.

41. A biassing device according to claim 35 wherein said body member has at least one further bore therein, and wherein said retaining means comprises at least one elongated member slideably received in said at least one further bore, said elongated member having second abutment means for engaging said first abutment means of said body member.

42. A biassing device according to claim 35 wherein said retaining means comprises a telescoping elongated retaining means.

43. A biassing device according to claim 42 wherein said telescoping elongated retaining means comprises a first elongated member having a hollow portion, and a second elongated member slideably received in said hollow portion of said first elongated member, and means coupled to said members for preventing said second elongated member from sliding completely out of engagement with said first member.

44. A biassing device according to claim 43 wherein said first member has an elongated slot therein, and said second member has a pin-like member protruding therefrom and engageable in said elongated slot, said elongated slot having a termination point which is engageable with said pin-like member to prevent disengagement of said first and second members.

45. A biassing device according to claim 43 wherein said second member has an axial groove therein which terminates short of the end of said second member, and said first member has a pin-like member therein which extends into said hollow portion and engages in said groove, said pin-like member engaging an end wall of said groove proximate the end of said second member to prevent disengagement of said first and second members.

46. A biassing device according to claim 34 wherein said retaining means comprises second abutment means coupled to said elongated threaded member for abutting said first abutment means preventing unthreading of said elongated threaded member from said at least one body member.

47. A biassing device according to claim 46 wherein said second abutment means comprises an enlarged end portion of said threaded member.

48. A biassing device according to claim 46 wherein said second abutment means comprises an outwardly bulged end portion of said threaded member.

49. A biassing device according to claim 46 wherein said threaded bore of said body member extends only partially through said body member and communicates with a further bore which has a larger internal dimension than said threaded bore, the transition between said threaded bore and said further bore comprising said first abutment means, and said second abutment means of said retaining means comprises an enlarged portion at the end portion of said threaded member which engages said threaded bore of said body member, said enlarged portion being passable through said further larger internal bore and being non-passable through said threaded bore.

50. A biassing device according to claim 49 wherein said further bore has an internal thread thereon and said enlarged portion has an external thread thereon which threadably engages the internal thread of said larger bore.

51. A biassing device according to claim 46 wherein said threaded bore of said at least one body member extends only partially through said at least one body member and communicates with a further bore which has a smaller internal dimension than said threaded bore, and said retaining means comprises an enlarged threaded portion at the end portion of said elongated threaded member which engages said threaded bore of said at least one body member, said enlarged portion being passable through said threaded bore and being non-passable through said smaller bore.

52. A biassing device according to claim 34 wherein said threaded bore of said body member extends only partially through said body member and communicates with a further bore which has a larger internal dimension than said threaded bore, the transition between said threaded bore and said further bore comprising said first abutment means, and said second abutment means of said retaining means comprises an outwardly extending portion at the end portion of said threaded member which engages said threaded bore of said body member, said outwardly extending portion being passable through said further internal bore and being non-passable through said threaded bore.

53. A biassing device according to claim 52 wherein said further bore has an internal thread thereon and said enlarged portion has an external thread thereon which threadably engages the internal thread of said larger bore.

54. A biassing device according to claim 34 wherein said threaded bore of said at least one body member extends only partially through said at least one body member and communicates with a further bore which has a smaller internal dimension than said threaded bore, and said retaining means comprises an enlarged threaded portion at the end portion of said elongated threaded member which engages said threaded bore of said at least one body member, said enlarged portion being passable through said threaded bore and being non-passable through said smaller bore.

55. An orthodontic biassing device comprising:
a single body member having a threaded bore directly formed therein;
an elongated threaded member which is threadably engaged in said threaded bore of said body member;
said single body member having a further bore directly formed therein and stop means integral with said single body member and being in communication with said further bore; and
an elongated member slidably mounted in said further bore of said single body member and having means thereon for engaging said stop means to restrict relative movement between said elongated member and said body member, said elongated member having means in the vicinity of the other end thereof for applying an orthodontic force to a tooth; and
means coupling said elongated threaded member to said force applying means such that said threaded member, upon being rotated relative to said body member, causes relative movement between said body member and said elongated member and force applying member.

56. An orthodontic biassing device comprising:
two body members adapted to engage one or more teeth and to be spaced from each other, each of said body members having a threaded bore therein, said threaded bores being oppositely threaded;
an elongated threaded member having oppositely threaded end portions which are respectively threadably engaged in the threaded bores of said body members to selectively expand or contract the spacing between said body members; and retaining means cooperating with at least one of said body members for limiting relative movement between said elongated threaded member and said at least one body member when the spacing between said body members is expanded to a predetermined spacing, thereby preventing disengagement of said elongated threaded member from said body members, said retaining means comprising said oppositely threaded end portions of said elongated threaded member having respectively different lengths, whereby when the shorter threaded portion is unthreaded from said at least one body member, the longer threaded portion remains threaded in the other of said body members, thereby preventing disengagement of said elongated threaded member from said at least one body member.

* * * * *